United States Patent [19]

Clarke

[11] 4,139,307
[45] Feb. 13, 1979

[54] SURFACE INSPECTION SYSTEMS

[75] Inventor: Graham M. Clarke, Edinburgh, Scotland

[73] Assignee: Ferranti Limited, Hollinwood, England

[21] Appl. No.: 799,926

[22] Filed: May 24, 1977

[30] Foreign Application Priority Data

May 27, 1976 [GB] United Kingdom ............... 22088/76

[51] Int. Cl.² ............................................. G01N 21/30
[52] U.S. Cl. .................................... 356/446; 250/571; 356/431
[58] Field of Search ............... 356/160, 167, 199, 200, 356/209, 210, 212, 237; 250/571, 572

[56] References Cited

U.S. PATENT DOCUMENTS

| 3,922,093 | 11/1975 | Dandliker et al. | 356/200 |
| 3,984,189 | 10/1976 | Seki et al. | 356/210 |

FOREIGN PATENT DOCUMENTS 1442134  5/1966  France ..................................... 356/237

Primary Examiner—Paul A. Sacher
Assistant Examiner—R. A. Rosenberger
Attorney, Agent, or Firm—Cameron, Kerkam, Sutton, Stowell & Stowell

[57] ABSTRACT

A surface inspection system has a light beam repetitively scanning a surface and a receiver located to receive light specularly (directly) reflected. The receiver has an enclosure with a wall containing a plurality of slits by which reflected light can reach a detector in the enclosure. The slits are arranged to cause the detector to produce a series of pulses throughout the scan, each pulse providing an instantaneous picture of the surface gloss in terms of an intensity distribution, the half width of each pulse is measured to give an indication of any variation from the half width of the distribution for a known surface gloss.

9 Claims, 10 Drawing Figures

SURFACE INSPECTION SYSTEMS

This invention relates to surface inspection systems and in particular to inspection systems for measuring the gloss of a surface.

The gloss of a surface may be defined as, and is used in this specification to mean, the extent to which a beam of light reflected from the surface is concentrated in the direction that a reflected beam would follow if the surface were a perfect reflector.

Inspection systems for measuring the gloss of a surface are known in which a beam of light is projected onto the surface; a receiver having a small aperture is located at the specular angle of reflection in the plane of the incident beam to receive the maximum amount of reflected light and moved out of the plane on both sides thereof to collect light scattered by the surface. The intensity of light received as a function of the angle out of the plane of the true specular reflection falls at a rate dependent on the gloss of the surface but retains the general shape of a rounded pulse.

It will be appreciated that such a measurement may take a considerable time requiring the surface to remain stationary for the duration and is not suitable for monitoring the gloss of a large area of surface at a number of points thereon.

An alternative method measures the light simultaneously at more than one angular position but must be completely duplicated to measure at more than one point requiring a plurality of receivers and suffers from inaccuracy due to loss of detail from distribution of the light between receivers and interaction due to simultaneous reception.

It is an object of the present invention to provide an inspection system of simple construction for measuring the gloss of a surface at a plurality of points thereon at high speed.

According to the present invention a surface inspection system for measuring the gloss of a surface caused to move past the system includes a transmitting station from which a beam of light is directed onto the surface and caused to scan repetitively across the surface, a receiving station comprising a detector of light, an enclosure containing the detector extending across the surface and having a plurality of slits in one wall thereof by which light may reach the detector, the one wall extending so that the slits are arranged to receive light reflected at the specular angle and the slits being spaced apart such that the reflected beam enters each slit in turn to produce from the detector a succession of detector pulses each having the characteristic features of the gloss of the surface under test, and measuring means operable to measure the duration of the detector pulses at a predetermined level with respect to the amplitude of each pulse to produce a signal indicative of the gloss of the part of the surface giving rise to that pulse.

Embodiments of the invention will now be described by way of example with reference to the accompanying drawings, in which.

Figure 1:
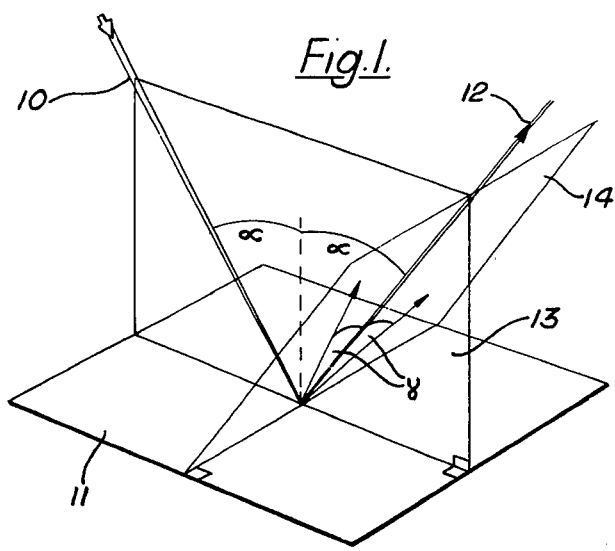
FIG. 1 is an illustration of light reflected from a plane surface and the angles involved in gloss measurement.
Figure 2:
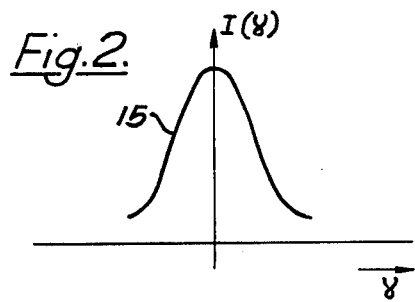
FIG. 2 shows the variation of intensity of reflected light with deviation from the plane of the incident beam.

Referring now to FIG. 1, a beam of light 10 incident on a plane surface 11 having a high gloss value is reflected as a beam 12 the incident and reflected beams being substantially at the same angle $\alpha$ to the normal to the plane 11 and substantially in the same plane 13.

Where the gloss is less than perfect there will be components of light reflected at angle $\pm \alpha$ in the plane 13 and at $\pm \gamma$ out of the plane, that is, in the plane 14. If a detector of reflected light is moved in the plane 14 and the signal produced is directly proportional to the intensity I of light received then a plot of $I(\gamma)$ against $\gamma$ is as shown in FIG. 2, taking the form of a rounded pulse. The pulse shape is a characteristic of the surface and it will be appreciated that for a particular amplitude of pulse the narrower the pulse at a given height the greater the surface gloss.

Figure 3:
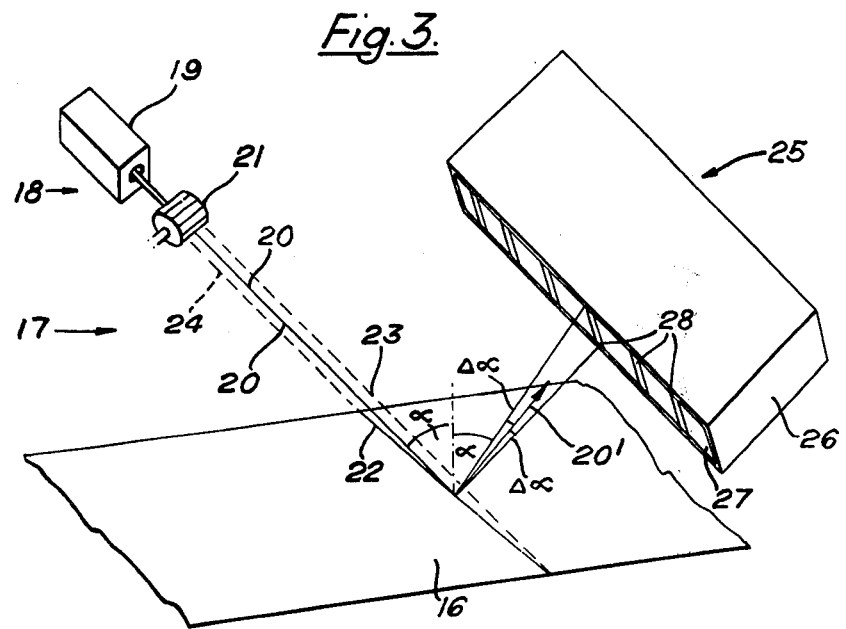
FIG. 3 is a simplified perspective view of an inspection system according to the present invention.
Figure 4:
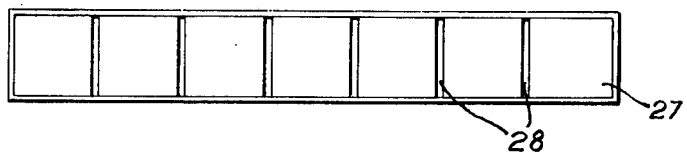
FIG. 4 is a plan view of one form of wall of the enclosure of FIG. 3 showing an array of parallel extended slits.

Referring now to FIG. 3 the present invention uses this property for making large numbers of measurements by moving a web of material 16 past the measuring system. The system 17 comprises a transmitting station 18 containing a light source 19, conveniently a low power gas laser producing a continuous beam 20, and a rotatable multifaceted mirror 21 which causes the beam 20 to scan the surface 16 along a line 22 extending transversely to the direction of motion of the web between the limits 23 and 24. Light is incident on the surface at angle $\alpha$ to the normal thereto which angle varies only slightly throughout the scan. Light reflected from the surface 20' is mainly at an equal angle $\alpha$ to the normal. A receiving station 25 comprising an enclosure 26 containing a photodetection means (not shown) is located such that the reflected beam 20' is incident upon the wall 27 of the enclosure throughout the scan. The wall 27 shown also in FIG. 4 contains a plurality of slits 28 by which the beam can enter the enclosure at a plurality of locations throughout the scan. The slit dimensions are chosen such that the slit length can accept all light reflected between the angle $(\alpha \pm \Delta\alpha)$ in the direction of motion of the surface but restricted in the direction of scan to define a resolution of about one degree. Such resolution may be obtained by a slit width of 1.7 mm when the receiver wall 24 is located 100 mm from the surface.

Figure 5:
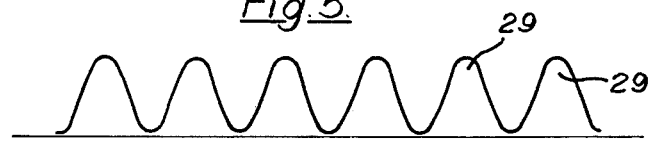
FIG. 5 is the waveform of a detector signal for a single scan of the surface.
Figure 6A:
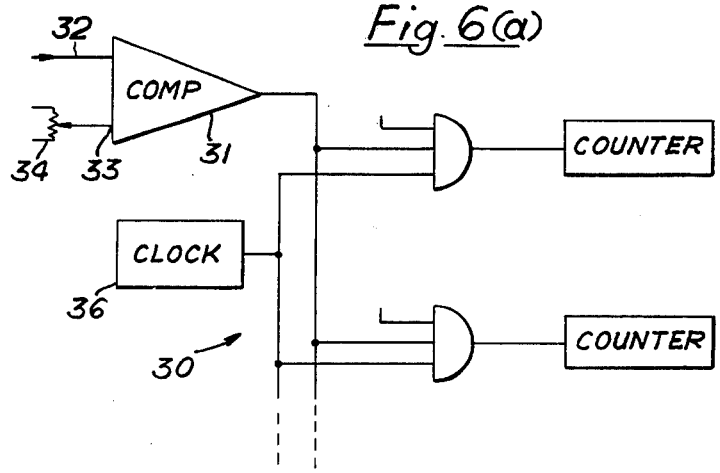
FIG. 6(a) is a circuit diagram of part of the measuring means.
Figure 6B:
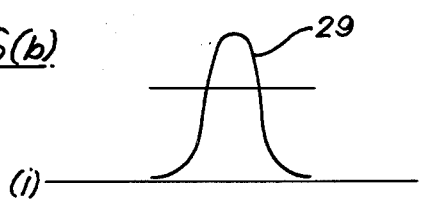
FIG. 6(b) shows waveforms appearing in the circuit of FIG. 6(a)
Figure 6B:
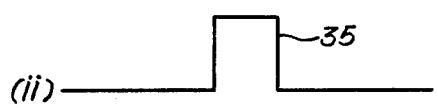
Figure 6B:

In operation as the beam 20 sweeps across the surface the reflected beam 20' enters the enclosure 26 through each slit 28 in turn and causes to be produced from the detector a signal comprising a series of pulses 29 having the waveform shown in FIG. 5.

Each pulse 29 corresponds to a slit 25 and in shape has the characteristic features of the pulse of FIG. 2. It will be appreciated that in order to obtain for processing a series of district pulses the spacing between adjacent slits must be controlled. It has been found that on all but relatively matt materials the receiver response to reflected light is sufficiently low at 45° from the maximum to permit spacing of the receiver from the material. For example, for a 600 mm. web with 100 mm. receiver to web spacing six parallel slits can be employed.

Referring to FIG. 6 the output signal of the detection means is fed to the measuring means 30 by way of a gain adjusting system (not shown) to produce equal amplitude responses throughout the scan. This may be achieved by the use of neutral density filter arrangements or a digital stored profile technique described in copending application Ser. No. 794,511, filed May 6, 1977, to remove receiver variations and variations due to changing angle of incidence. The measuring means comprises a comparator 31 having a first input 32 arranged to receive the detector signal comprising a succession of pulses 29 of the detector signal (shown at FIG. 6(b)(i)) and a second input 33 connected to a threshold voltage set at half the amplitude of the pulse 29. The comparator is arranged to produce a comparator signal only when the detector signal is in excess of the threshold value, which comparator signal comprises a rectangular pulse 35 shown in FIG. 6(b) (ii). A clock pulse generator 36 provides a train of clock pulses by way of line 37 to a series of AND gates 38, 39 . . . one for each slit. Each gate feeds to an individual counter 40, 41 . . . of the clock pulses. The outputs of the comparator and clock are fed to input at each gate another input being fed with a gating signal from control means (not shown) which opens each gate in turn for the duration of the comparator output pulse to pass clock pulses to the counter (FIG. 6(b)(iii)).

The number of clock pulses counted in each counter in a single scan can be related to the part of the surface from which the light was reflected and each total provides a measure, by the width of the detector pulse at its half-amplitude, of the gloss of the surface.

It will be appreciated that the width of the pulse may be measured at other than its half-amplitude and by means other than counting pulses. Width measurement may be accomplished in analogue form using integrators, or comparison may be made with a standard form of detector pulse by displaying the detector signal on a C.R.T. and superimposing a graticule carrying the desired pulse shape.

Figure 7:
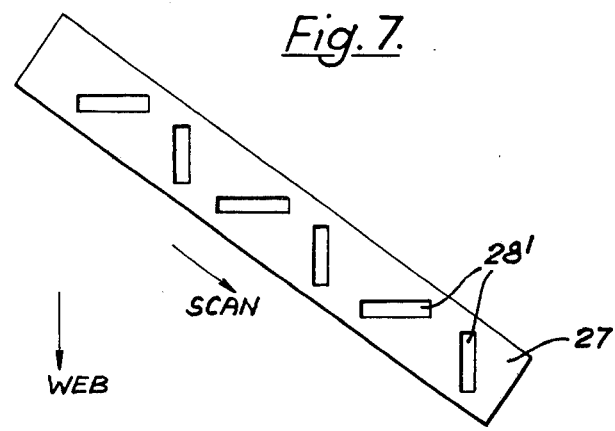
FIG. 7 is a plan view of an alternative form of enclosure wall.

In a system as described above all of the slits 25 of the enclosure wall are arranged to provide information on the surface gloss in a direction transversely to the motion of the web. Where the surface displays an anisotropic response, that is, the scattering of light is dependent upon orientation of the surface with respect to the incident beam, the system may be modified as shown in FIG. 7 by providing the enclosure wall 27 with alternate slits 28' at an angle to each other. Typically, a rolled surface will be coarsest across its width and the slits are arranged orthogonally to each other at 45° to the length of the wall. The enclosure is located with respect to the surface such that the beam scans the surface at 45° to the detection of motion of the surface so that for a complete scan, alternate slits provide information on the gloss of the surface for the component of incident beam reflected along, and orthogonal to, the direction of travel of the surface. Where the surface is coarsest at any other angle to the direction of motion the angle between adjacent slits is modified to be along maximum and minimum pattern widths as required.

Figure 8:
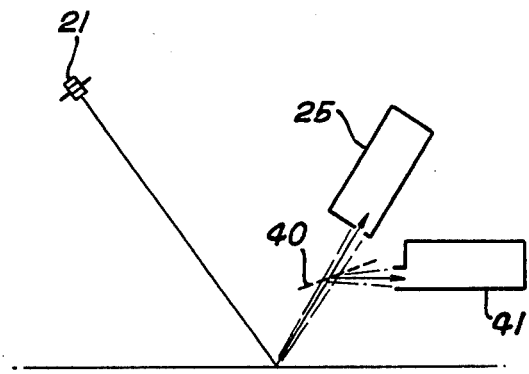
FIG. 8 is a sectional view through a surface inspection system according to the present invention and including a defect measuring arrangement.
Figure 9:
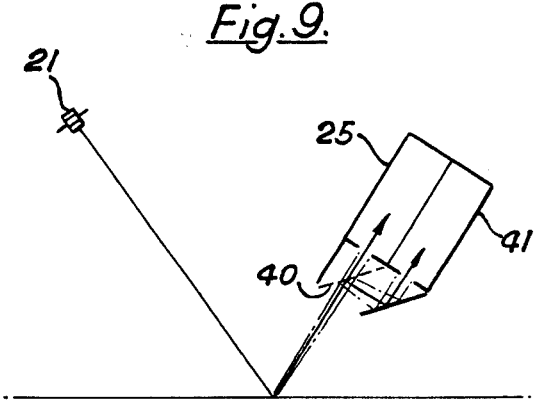
FIG. 9 is a sectional view through an alternative form of the surface inspection system of FIG. 8.

FIGS. 8 and 9 show alternative arrangements of the surface inspection system in which gloss measurement is combined with surface defect detection. The beam reflected from the surface is passed through a beam splitter 40 which directs a part of the beam to a defect receiver 41 which collects all of the light in the part of the beam incident on it and which is responsive to a change in the level of light received throughout the scan to indicate a surface defect affecting the local reflectivity of the surface. In FIG. 8 the "defect" receiver is shown as a separate enclosure and in FIG. 9 the two enclosures are integrated into a single unit.

What I claim is:

1. A surface inspection system for measuring the gloss of a surface caused to move past the system including a transmitting station from which a beam of light is directed onto the surface and caused to scan repetitively across the surface, a receiving station comprising a detector of light, an enclosure containing the detector extending across the surface and having a plurality of slits in one wall thereof by which light may reach the detector, the one wall extending so that the slits are arranged to receive light reflected at the specular angle and the slits being spaced apart such that the reflected beam enters each slit in turn to produce from the detector a succession of detector pulses each having the characteristic features of the gloss of the surface under test, and measuring means operable to measure the duration of the detector pulses at a predetermined level with respect to the amplitude of each pulse to produce a signal indicative of the gloss of the part of the surface giving rise to that pulse.

2. A surface inspection system as claimed in claim 1 in which the transmitting station is arranged to cause the beam of light to scan the surface transversely to the direction of motion of the surface and the slits are arranged along the direction of scan of the beam, each slit extending transversely to the direction of scan of the beam and having a predetermined width in the direction of scan.

3. A surface inspection system as claimed in claim 2 in which the predetermined width of the slit subtends an angle of the reflected beam of substantially one degree.

4. A surface inspection system as claimed in claim 1 in which the transmitting station is arranged to cause the beam of light to scan the surface at substantially 45° to the direction of motion of the surface, the enclosure extending along the direction of scan and having alternate slits arranged at right angles to each other such that some extend along the direction of motion of the surface and the others extend transversely thereto, each slit having a predetermined width at substantially 45° to the direction of scan.

5. A surface inspection system as claimed in claim 1 in which the separation of slits is chosen such that when one slit receives directly light reflected at the specular angle adjacent slits are unable to receive light scattered in the plane of the specularly reflected beam at an angle of less than 45°.

6. A surface inspection system as claimed in claim 1 in which the measuring means comprises threshold means responsive to detector pulses in excess of a predetermined threshold value to count a plurality of clock pulses, the number of clock pulses counted for each detector pulse being indicative of the gloss of the surface.

7. A surface inspection system as claimed in claim 6 in which threshold means comprises a comparator operable to compare the detector signal with a threshold voltage and to provide a comparator signal while the detector signal exceeds the threshold voltage, a source of clock pulses, a plurality of gates individual gates being associated with individual slits and to which gates the comparator signals and clock pulses are fed, control means operable to open each gate in turn as the reflected beam strikes the associated slit to enable that gate to pass clock pulses for the duration of the comparator signal and counting means associated with each gate to count said clock pulses to provide by the total an indication of the gloss of the surface.

8. A surface inspection system as claimed in claim 7 in which the threshold voltage is set to substantially half of the amplitude of the detector signal.

9. A surface inspection system as claimed in claim 1 including a surface defect detector responsive to a change in intensity of the reflected beam to provide a signal indicative of a surface blemish causing absorption or deflection of the beam and beam splitting means located so as to direct light reflected from the surface both to the receiving station and to the surface defect detector.

* * * * *